(12) United States Patent
Ma et al.

(10) Patent No.: US 10,017,457 B2
(45) Date of Patent: Jul. 10, 2018

(54) CONTINUOUS SYNTHESIS OF ISOOCTYL NITRATE IN A FLOW REACTOR

(71) Applicant: Corning Incorporated, Corning, NY (US)

(72) Inventors: Bing Ma, Shanghai (CN); Wei Shen, Changzhou (CN); Yanhua Wang, Changzhou (CN); Mo Zhang, Changzhou (CN)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 15/123,100

(22) PCT Filed: Mar. 5, 2015

(86) PCT No.: PCT/US2015/018876
§ 371 (c)(1),
(2) Date: Sep. 1, 2016

(87) PCT Pub. No.: WO2015/134703
PCT Pub. Date: Sep. 11, 2015

(65) Prior Publication Data
US 2017/0066710 A1   Mar. 9, 2017

(30) Foreign Application Priority Data

Mar. 7, 2014 (CN) .......................... 2014 1 0082963

(51) Int. Cl.
*C07C 201/02* (2006.01)
(52) U.S. Cl.
CPC .................. *C07C 201/02* (2013.01)
(58) Field of Classification Search
None
See application file for complete search history.

(56) References Cited

U.S. PATENT DOCUMENTS

| 4,497,905 A | 2/1985 | Nozaki |
| 4,853,157 A | 8/1989 | Stiff |
| 5,411,989 A | 5/1995 | Michel et al. |
| 7,632,960 B2 | 12/2009 | Pohlmann et al. |
| 9,365,488 B2 | 6/2016 | Xu et al. |
| 2007/0129563 A1* | 6/2007 | Pohlmann ............. C07C 201/02 558/480 |

FOREIGN PATENT DOCUMENTS

| CN | 1031525 A | 3/1989 |
| CN | 101462962 A | 6/2009 |
| CN | 101698646 A | 4/2010 |
| WO | 2012152438 A1 | 11/2012 |

OTHER PUBLICATIONS

European Patent Office; International Search Report and Written Opinion of International Application Serial No. PCT/US2015/018876, filed Mar. 5, 2015; dated Jun. 5, 2015; pp. 1-8.

* cited by examiner

Primary Examiner — Samantha L Shterengarts
(74) Attorney, Agent, or Firm — Gregory V. Bean

(57) ABSTRACT

A process for synthesizing isooctyl nitrate in a continuous flow reactor comprises flowing a H2SO4-HNO3 mixture within a flow reactor, flowing isooctyl alcohol into said flow reactor so as to mix the isooctyl alcohol with the H2SO4-HNO3 mixture and produce a reaction mixture stream flowing in said reactor, maintaining the reaction mixture stream flowing in said flow reactor at a reaction temperature within in the range −10° to 35° C. inclusive, and wherein the residence time of the reaction mixture stream in the flow reactor is greater than or equal to 5 seconds and less than or equal to 40 seconds, and wherein the H2SO4 of the H2SO4-HNO3 mixture is H2SO4 having a concentration of in the range of 85 to 95% inclusive, more desirably 88 to 92% inclusive, most desirably of 90%.

13 Claims, 2 Drawing Sheets

CONTINUOUS SYNTHESIS OF ISOOCTYL NITRATE IN A FLOW REACTOR

CROSS-REFERENCE TO RELATED APPLICATION

This application claims the benefit of priority under 35 U.S.C. § 371 of International Patent Application Serial No. PCT/US15/18876, filed on Mar. 5, 2015, which claims the benefit of priority under 35 U.S.C. § 119 of Chinese Patent Application Serial No. 201410082963.0, filed on Mar. 7, 2014, the contents of which are relied upon and incorporated herein by reference in their entireties.

BACKGROUND

The disclosure relates to the continuous synthesis of isooctyl nitrate in flow reactors, and more particularly to the continuous synthesis of isooctyl nitrate in a flow reactor with residence time of at least 5 seconds utilizing 90% H2SO4.

Isooctyl nitrate, also known as 2-ethyl hexyl nitrate, is an important additive to improve cetane number (CN) of diesel. Higher CN decreases the ignition point, speeding up ignition, improving engine power while reducing fuel consumption. Efficient, safe and environmentally friendly production of isooctyl nitrate is accordingly desirable.

SUMMARY

A process for synthesizing isooctyl nitrate in a continuous flow reactor comprises flowing an H2SO4-HNO3 mixture within a flow reactor and flowing isooctyl alcohol into said flow reactor so as to mix the isooctyl alcohol with the H2SO4-HNO3 mixture and produce a reaction mixture stream in said flow reactor at a reaction temperature within in the range −10° to 35° C. inclusive. Further, the residence time of the reaction mixture stream in the flow reactor is within the range of 5 to 40 seconds, inclusive, and the H2SO4 of the H2SO4-HNO3 mixture has a concentration within the range of 85 to 95% inclusive H2SO4. In additional or alternative embodiments, the H2SO4 of the H2SO4-HNO3 mixture has a concentration within the range of 88 to 92% inclusive H2SO4, or a concentration of 90% H2SO4.

A further alternative or additional aspect (in the form of additional steps that may desirably be included with steps of any or all other embodiments) comprises capturing post-reaction H2SO4 and reusing the captured H2SO4 in the H2SO4-HNO3 mixture.

The present disclosure provides a method for synthesizing isooctyl nitrate in a continuous flow reactor in which very high conversion (of at least 99.5% and up to 100%) and yield (of at least 99% and up to 100%) may be achieved using less-concentrated H2SO4 in place of the typical 98% H2SO4, such as H2SO4 in the range of 85 to 95% inclusive, desirably 88 to 92% inclusive, most desirably 90% (to within typical industrial tolerances). This allows for recovery and re-use of H2SO4, thus decreasing the cost of the process and lessening the environmental effects thereof.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiment(s), and together with the description serve to explain principles and operation of the various embodiments.

DETAILED DESCRIPTION

Figure 1:
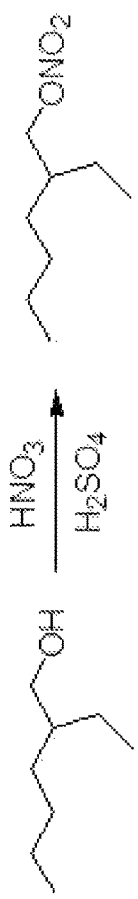
FIG. 1 is a diagram of the reaction to be performed by the process of the current disclosure.
Figure 2:
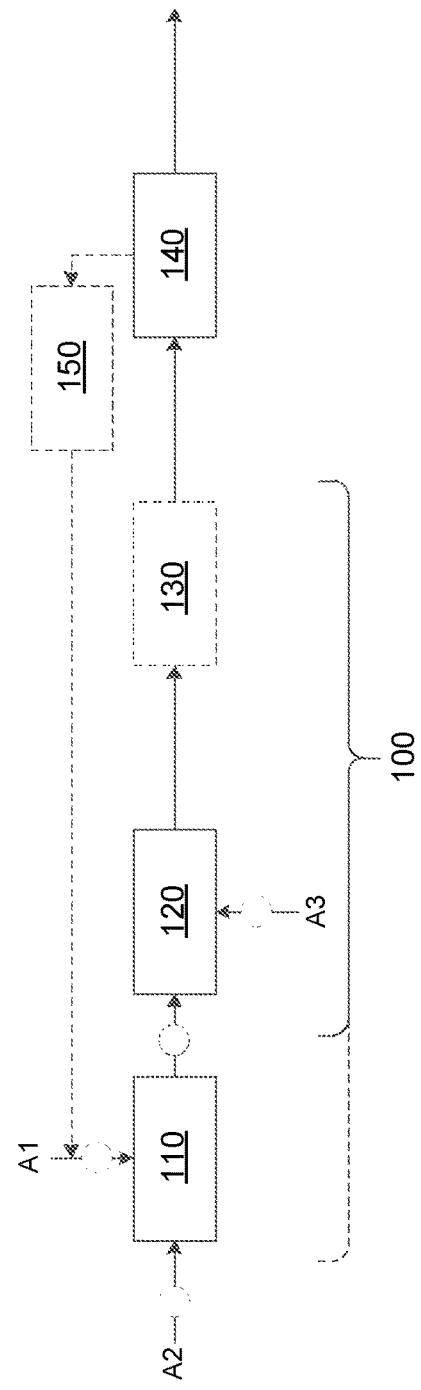
FIG. 2 is a process diagram of an embodiment of a process according to the present disclosure.

The present disclosure provides a continuous process for production of isooctyl nitrate from isooctyl alcohol and an HNO3-H2SO4 acid mixture in a flow reactor. A diagram of the reaction is shown in FIG. 1, and a process diagram 200 is shown in FIG. 2, including a flow reactor 100 and additional process components. Three chemicals, H2SO4 (feed A1), HNO3 (feed A2) and isooctyl alcohol (feed A3), are desirably dosed separately by the use of pulsation-free pumps. In that case, the HNO3-H2SO4 acid mixture is prepared in the flow reactor 100 by flowing the feeds A1 and A2 together so as to mix the acids in reactor module 110. Alternatively, the HNO3-H2SO4 acid mixture may be prepared in an upstream batch, and then dosed with one pump, in which case module 110 may represent a batch processing source 110 for the acid mixture (and thus not a part of the flow reactor 100), which mixture is flowed into (pumped by the single pump represented in dashed outline) into the flow reactor 100, at module 120, and the pumps shown on feeds A1 and A2 may be unnecessary. In either case, lower-concentration H2SO4 is used, rather than the typical high strength 98% H2SO4, as a component of the acid mixture. The H2SO4 used may have a concentration in the range of 85 to 95% inclusive, desirably 88 to 92% inclusive, most desirably 90%, to within typical industrial tolerances. In either case (whether acid mixing takes place in the flow reactor 100 or not) the acid mixture is flowed within the flow reactor 100 in this embodiment, in (and into) module 120.

Isooctyl alcohol is also flowed into the flow reactor 100, as feed A3 into module 120 in this embodiment, so as to mix the isooctyl alcohol with the H2SO4-HNO3 mixture and produce a reaction mixture stream flowing in the reactor 100, beginning within module 120 in the embodiment shown.

The reaction time in the flow reactor (the "dwell time" or "residence time" after first contact of the alcohol and the acid mixture) is controlled to be in the range of from 5 to 40 seconds, inclusive, desirably in the range of from 10 to 20 seconds, inclusive. If additional volume (length) of flow path is needed within the flow reactor 100 in order to achieve such residence time simultaneously with adequate flow rates for desirable rates of production and mixing, one or more additional modules 130 (shown in dashed outline because it is optional) may be used downstream of module 120. The reaction mixture stream is desirably flowed within a passage shaped to induce mixing throughout the duration of the residence time. In other words, in the embodiment shown, downstream of the contact point of the acid mixture and the alcohol within module 120, the flow passage is desirably shaped to induce mixing along its whole length, both within module 120 and within subsequent flow reactor module(s) 130, if any.

While the acid mixture and the alcohol are mixing and then flowing together in the reactor 100, the temperature range of the process is maintained at a temperature within the range of from −10 to 35° C., inclusive, desirably within 5° to 15° C., inclusive. This may be achieved by the use of chilled thermal control fluid circulated around or within the reactor 100, desirably around or within the module 120 and around or within subsequent flow reactor module(s) 130, if any, in parallel.

Flow rate ranges may extend from 0.25 mol/minute for the alcohol reactant (such as in an Advanced-Flow™ reactor from Corning Incorporated assembled from "G1" flow modules) to 16 mol/minute for the alcohol reactant (such as in an Advanced-Flow™ reactor from Corning Incorporated assembled from larger "G4" flow modules). As mentioned above, the reactor is desirably of such design that the reaction mixture stream is flowed within a passage shaped to induce mixing throughout the duration of the residence time. System pressure under these conditions and in the "G1" and "G4" flow reactors (as described in the examples below) ranges from 0.2 MPa to 1 MPa, and a safe and stable process is achieved, as evidenced by a lack of variation in system pressure, product temperature, or product color.

After the reaction, the crude reacted solution is then separated in separator/separation process 140 to obtain the organic phase, which may be washed and neutralized with aqueous NaHCO3. After drying, and filtration, pure product may then be obtained. Greater than 99.5% of conversion was achieved (and as much as 100%), and the yield better than 99% (and as much as 100%) was achieved by the disclosed method.

Because the reaction temperature is limited to temperatures of 35° C. and below, and because the reaction time (residence time) is long (from 5 to 40 seconds, desirably 10 to 20), the reaction is slower and easier to control, and thermal runaway is prevented. Given that such excellent conversion and yield are achieved with lower-concentration H2SO4, such as only 90% H2SO4 (rather than 98%), post-reaction H2SO4 may optionally be captured in capture device/process 150. Captured H2SO4 may then be reused in the H2SO4-HNO3 mixture as a part of the disclosed process, as indicated by the dashed path from capture device/process 150 to feed A1, such as by purifying the captured H2SO4 (which will generally be at weaker strength than that used at the start of the process) or by mixing some of the captured H2SO4 with higher strength H2SO4 to provide the desired starting strength. Such reuse can reduce the cost and improve the environmental performance of the process.

Note that processes and/or steps not performed within the flow reactor 100, such as separation process/device 140 and (optional) capture process/device 150, as well as the acid mixing in device 110, may be either flow-type devices/processes or batch-type, as desired or as appropriate.

As a further option flowing the H2SO4-HNO3 mixture within a flow reactor 100 may also include bringing the H2SO4-HNO3 mixture to, or maintaining the H2SO4-HNO3 mixture at, a temperature within the range of −10 to 35° C. inclusive, while flowing the H2SO4-HNO3 mixture within the flow reactor. If, as is desirable, the H2SO4-HNO3 mixture is prepared upstream in a part of the flow reactor 100 (namely, in module 110), then modules 110 may also be provided with thermal control fluid circulated around or within the module 110. Similarly, the isooctyl alcohol may be brought to and/or maintained at a temperature within the range of −10 to 35° C. inclusive, before or while it is flowed within the flow reactor 100.

The flow rates of the acid mixture and alcohol are desirably chosen to result in a molar ratio of H2SO4 to isooctyl alcohol, in the reaction mixture stream, within the range of 1.5:1 to 2:1 inclusive. The flow rates of the acid mixture and alcohol are also desirably chosen to result in a molar ratio of HNO3 to isooctyl alcohol, in the reaction mixture stream, of 1:1.

In addition to allowing use of less-concentrated H2SO4, which allows for economically feasible recovery and recycling of H2SO4, the present process can and desirably does achieve conversion of 100% and yield of greater than 99.5%, desirably 100%.

EXAMPLES

Various embodiments will be further illustrated in or by the following examples. The reactors 100 used in the examples below are shown diagrammatically in FIGS. 3 and 4.

Figure 3:
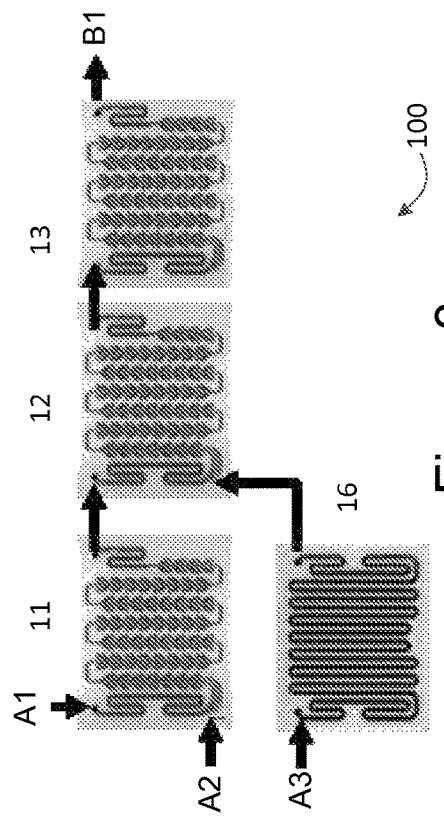
FIG. 3 is a diagram of an embodiment of a flow reactor useful in practicing processes of the current disclosure.

FIG. 3 shows a flow reactor 100 comprised, in this embodiment, of modules 11, 12, 13, and 16 of the "G1" size and type available from Corning Incorporated. As shown in FIG. 3, feeds A1 and A2, 90% H2SO4 and 98% HNO3 respectively, are flowed into a flow reactor 100, in this case comprised of "G1" modules from Corning Incorporated. Module 11 mixes the acids as they flow therein, and is actively cooled. A module 16 is employed to receive feed A3, the isooctyl alcohol, and is desirably also cooled to provide "precooling" of the alcohol. The H2SO4-HNO3 mixture from module 11, along with the optionally pre-cooled alcohol from module 16, is flowed into the module 12 which serves to mix the isooctyl alcohol and the acid mixture together. Additional residence volume/residence time is provided by module 13. As seen in the flow paths shown in modules 12 and 13, the reaction mixture stream flows within a passage shaped to induce mixing throughout the duration of the residence time. Crude product then emerges at the outlet B1.

Figure 4:
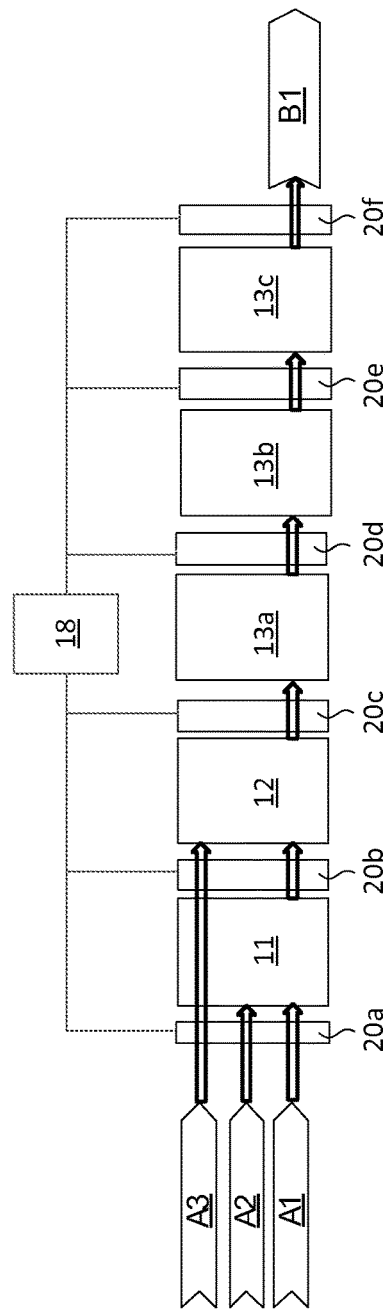
FIG. 4 is a diagram of another embodiment of a flow reactor useful in practicing processes of the current disclosure.

FIG. 4 is a diagrammatic representation of a flow reactor 100 comprised, in this embodiment, of modules 11, 12, 13a, 13b, and 13c of the "G4" size and type available from Corning Incorporated. As shown in FIG. 4, heat exchange structures 20a-20f are layered around in in-between the modules 11, 12, 13a, 13b, and 13c to provide the desired thermal control for the reaction. A chiller 18 may be used to provide chilled thermal control fluid to the heat exchange structures 20a-20f, as shown. Feeds A1 and A2, 90% H2SO4 and 98% HNO3 respectively, are flowed into the flow reactor 100 comprised of "G4" modules. Module 11 mixes the acids as they flow therein. Feed A3, the isooctyl alcohol, is passed more or less directly through the module 11, without contacting the H2SO4-HNO3 mixture therein. The H2SO4-HNO3 mixture from module 11 and the alcohol are flowed into the module 12 which serves to mix the isooctyl alcohol and the acid mixture together. Additional residence volume/residence time is provided by modules 13a, 13b, and 13c. Crude product then emerges at the outlet B1.

Comparative Example

A G1 Advanced-Flow™ reactor from Corning was configured and set up according to the description of FIG. 3. A pump for 98% HNO3 was set to 13.3 g/min (9.4 mL/min, 0.21 mol/min), and a pump for 98% H2SO4 was set to 39.9 g/min (21.7 mL/min, 0.40 mol/min). A pump for the alcohol was set to 27.4 g/min (33 mL/min, 0.21 mol/min), and the temperature of a chiller for the cooling fluid was set to 0° C. Samples were collected periodically after the system stabilized (at about 2 minutes). Gas Chromatography (GC) analysis showed a full conversion of the starting material, and the yield was 100%. With the an internal volume of 16 mL (2 modules), the retention time was (16 mL)/(64.1 mL/min)*60=15 s (or liquid space velocity of 240 h$^{-1}$).

Example 1

A G1 Advanced-Flow™ reactor from Corning was configured and set up according to the description of FIG. 3. A pump for 98% HNO3 was set to 15.7 g/min (11.2 mL/min, 0.25 mol/min), and a pump for 90% H2SO4 was set to 47.1 g/min (26.2 mL/min, 0.43 mol/min). A pump for alcohol was set to 33.2 g/min (40 mL/min, 0.25 mol/min), and the temperature of a chiller for the cooling fluid was set to 10° C. Samples were collected after the system stabilized (at about 2 minutes). GC analysis showed a full conversion of the starting material, and the yield was 100%. With internal volume of 16 mL (2 modules), the retention time was (16 mL)/(77.4 mL/min)*60=12 s (or liquid space velocity of 290 h$^{-1}$).

Example 2

A G4 Advanced-Flow™ reactor from Corning was configured and set up according to the description of FIG. 4. A pump for 98% HNO3 was set to 1.01 Kg/min (0.72 L/min, 16 mol/min), and a pump for 90% H2SO4 was set to 3.03 Kg/min (1.67 L/min, 27.8 mol/min), while a pump for alcohol was set to 2.08 Kg/min (2.5 L/min, 16 mol/min), with a the chiller temperature set to 10° C. Samples were collected after the system stabilized (at about 2 minutes). GC analysis showed a full conversion of the starting material, and the yield was 100%. With total internal volume of 1.0 L (4 modules), the retention time was (1.0 L)/(4.89 L/min) *60=12 s (or liquid space velocity of 290 h$^{-1}$).

As will be understood from the foregoing, the present disclosure provides a method for synthesizing isooctyl nitrate in a continuous flow reactor in which very high conversion and yield may be achieved using less concentrated H2SO4 in place of the typical 98% H2SO4, such as H2SO4 in the range of 85 to 95% inclusive, desirably 88 to 92% inclusive, most desirably 90% inclusive (within typical industrial tolerances). This allows for recovery and re-use of the H2SO4, thus decreasing the overall cost of the process and lessening the environmental effects thereof. Further advantages will be understood from the description. It will also be apparent to those skilled in the art that various modifications and variations can be made without departing from the spirit or scope of the claims.

What is claimed is:

1. A process for synthesizing isooctyl nitrate in a continuous flow reactor with 99% or greater conversion and 99% or greater yield, the process comprising:
   flowing a H2SO4-HNO3 mixture within a flow reactor;
   flowing isooctyl alcohol into said flow reactor so as to mix the isooctyl alcohol with the H2SO4-HNO3 mixture and produce a reaction mixture stream flowing in said reactor;
   maintaining the reaction mixture stream flowing in said flow reactor at a reaction temperature within in the range −10° to 35° C. inclusive,
   wherein the residence time of the reaction mixture stream in the flow reactor is in the range of 5 to 40 seconds, inclusive, and wherein the H2SO4 of the H2SO4-HNO3 mixture is 90% H2SO4.

2. The process according to claim 1 wherein the step of flowing a H2SO4-HNO3 mixture within a flow reactor comprises flowing a H2SO4 stream into a first inlet of the flow reactor and flowing a HNO3 stream into a second inlet of the flow reactor so as to mix the H2SO4 stream with the HNO3 stream and produce the mixed H2SO4-HNO3 stream flowing within said flow reactor.

3. The process according to claim 1 wherein the step of flowing a H2SO4-HNO3 mixture within a flow reactor comprises bringing the H2SO4-HNO3 mixture to, or maintaining the H2SO4-HNO3 mixture at, a temperature within the range of from −10° to 35° C. inclusive, while flowing the H2SO4-HNO3 mixture within the flow reactor.

4. The process according to claim 3, wherein the step of flowing isooctyl alcohol into said flow reactor further comprises bringing the isooctyl alcohol to, or maintaining the isooctyl alcohol at, a temperature within the range of from −10° to 35° C. inclusive, while flowing the isooctyl alcohol within the flow reactor.

5. The process according to claim 4, wherein the step of flowing isooctyl alcohol into said flow reactor so as to mix the isooctyl alcohol with the H2SO4-HNO3 mixture comprises flowing the reaction mixture stream within a passage having varying shape all along the length thereof so as to induce mixing throughout the duration of the residence time.

6. The process according to claim 1, wherein the step of flowing isooctyl alcohol into said flow reactor so as to mix the isooctyl alcohol with the H2SO4-HNO3 mixture comprises flowing the reaction mixture stream within a passage of varying shape all along the length thereof so as to induce mixing throughout the duration of the residence time.

7. The process according to claim 1, wherein the step of flowing a H2SO4-HNO3 mixture within a flow reactor comprises flowing a H2SO4-HNO3 mixture within a glass, glass-ceramic, or ceramic flow reactor.

8. The process according to claim 1 wherein the step of flowing a H2SO4-HNO3 mixture within a flow reactor comprises flowing at an acid mixture flow rate, the step of flowing isooctyl alcohol comprises flowing at an alcohol flow rate, and wherein said acid mixture flow rate and said alcohol flow rate result in a molar ratio of H2SO4 to isooctyl alcohol, in the reaction mixture stream, within the range of 1.5:1 to 2:1 inclusive.

9. The process according to claim 8 wherein the acid mixture flow rate and the alcohol flow rate result in a molar ratio of HNO3 to isooctyl alcohol, in the reaction mixture stream, of 1:1.

10. The process according to claim 8 wherein the alcohol flow rate is within the range of 0.25 to 16 moles per minute, inclusive.

11. The process according to claim 1 wherein the step of maintaining the reaction mixture stream flowing in said flow reactor within the range of from −10° to 35° C. inclusive comprises maintaining the reaction mixture stream flowing in said flow reactor at a temperature in the range of from 5 to 15° C., inclusive, and wherein the residence time of the reaction mixture stream in the flow reactor is greater than or equal to 10 seconds and less than or equal to 20 seconds.

12. The process according to claim 1 wherein the conversion is 100% and the yield is greater than 99.5%.

13. The process according to claim 1, wherein the process further comprises:
  capturing post-reaction H2SO4; and
  reusing the captured H2SO4 in the H2SO4-HNO3 mixture.

\* \* \* \* \*